(12) United States Patent
Birchak et al.

(10) Patent No.: US 6,310,426 B1
(45) Date of Patent: Oct. 30, 2001

(54) HIGH RESOLUTION FOCUSED ULTRASONIC TRANSDUCER, FOR LWD METHOD OF MAKING AND USING SAME

(75) Inventors: James R. Birchak, Spring; Alvin B. Miller, Alvarado; James W. Stroud, Houston, all of TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/353,198

(22) Filed: Jul. 14, 1999

(51) Int. Cl.[7] ................................................. H01L 41/08
(52) U.S. Cl. ............................................. 310/335; 310/346
(58) Field of Search ................................... 310/326, 327, 310/334–337, 346

(56) References Cited

U.S. PATENT DOCUMENTS

| | | | |
|---|---|---|---|
| 3,213,415 | 10/1965 | Moser et al. | 340/17 |
| 3,299,695 | * 1/1967 | Dickinson | 310/335 X |
| 3,433,461 | * 3/1969 | Scarpa | 310/335 X |
| 3,663,842 | * 5/1972 | Miller | 310/335 X |
| 3,832,655 | * 8/1974 | Yokoyama | 310/335 X |
| 4,450,540 | 5/1984 | Mallett | 367/41 |
| 4,493,062 | 1/1985 | Mallett | 367/32 |
| 4,507,582 | * 3/1985 | Glenn | 310/335 X |
| 4,509,360 | * 4/1985 | Erwin et al. | 310/335 X |
| 4,751,530 | * 6/1988 | Elrad et al. | 310/335 X |
| 4,805,156 | 2/1989 | Attali et al. | 367/35 |
| 4,869,278 | * 9/1989 | Bran | 310/335 X |
| 5,317,111 | 5/1994 | Orban et al. | 181/105 |
| 5,546,360 | * 8/1996 | Deegan | 310/335 X |
| 5,644,186 | 7/1997 | Birchak et al. | 310/337 |
| 5,726,951 | 3/1998 | Birchak et al. | 367/38 |
| 5,741,962 | 4/1998 | Birchak et al. | 73/152.16 |
| 5,763,773 | 6/1998 | Birchak et al. | 73/152.58 |

* cited by examiner

Primary Examiner—Mark O. Budd
(74) Attorney, Agent, or Firm—J. M. (Mark) Gilbreth; Mary A. Gilbreth; Gilbreth & Associates, P.C.

(57) ABSTRACT

The present invention relates to transducer packages which utilize lenses made of unpoled piezoelectric material or machined metal coupled to an impedance matched backing. The new transducer packages have minimal reverberation which allow for nearer standoff measurements, improved bond measurements, the ability to detect of thinner cement layers behind casing, and provide for better estimations of formation surface texture.

18 Claims, 7 Drawing Sheets

HIGH RESOLUTION FOCUSED ULTRASONIC TRANSDUCER, FOR LWD METHOD OF MAKING AND USING SAME

BACKGROUND OF THE INVENTION

1. Field of the Invention

The present invention relates to transducers, to tools utilizing such transducers and to methods of making and using transducers. In another aspect, the present invention relates to transducers for use in both logging while drilling ("LWD") and wireline applications, to tools utilizing such transducers and to methods of making and using such transducers. In even another aspect, the present invention relates to transducers with minimal reverberation, to tools utilizing such transducers and to methods of making and using such transducers.

2. Description of the Related Art

Well bores are lined with steel casing to prevent collapse of the bore while drilling and to prevent fluid communication between productive oil and gas bearing formations and nonproductive formations, such as those bearing water. A cement slurry is pumped downhole through this casing and displaced up into the annular space between the casing and the borehole wall where it hardens. Once the formations are separated by the cementing process, the desired formations are perforated for production.

Cracks or voids appearing in the cement between the casing and the borehole result in fluid communication problems. For example, water migrating into a producing is zone typically results in decreased production of hydrocarbons and contamination of equipment.

Acoustic imaging tools utilizing transducers are used to evaluate the condition of the cement by directing sonic pulses through the casing, through the cement and to the rock formations. In general, these tools consist of a transmitter capable of providing acoustical impulses, and at least one receiver responsive to acoustical energy, mounted on a support for movement through the length of the well bore. In pulse echo systems, the transmitter transducer is also the receiver. In pitch catch systems, the transmitter and receiver are spaced apart by a fixed distance. As the support is moved through the well bore, the energy from acoustic pulses periodically generated by the transmitter propagates to the wall, reflects (or refracts), propagates back to the receiver, and is picked up at the receiver. The amplitudes of the received signals are correlated with the depth in the well bore to provide a log indicating the qualities of the cement bonding to the bore as a function of depth in the well.

In order to evaluate formation, cement, casing and drilling fluids in wells, high resolution ultrasonic transducers are needed to identify features having small spatial size. This spatial resolution requires that the an transducer be responsive to signals separated by short time intervals. Broad frequency bandwidth is required. Because high frequency signals are highly attenuated, a highly damped pulse with a center frequency having a wavelength slightly smaller that the spatial features of interest is required. However, high damping requires that the transducer have very short reverberation time from any acoustic path within the transducer package.

The performance of logging while drilling caliper tools and the wireline circumferential scanning tools, pulse echo cement bond tools and cement imaging tools are degraded by reverberation in the transducers. If the reverberation can be minimized, the minimum inspection distance can be decreased, permitting nearer standoff measurements, improved bond measurements and detection of thinner cement layers behind casing. Improving the focusing of the open hole scanning transducers will give better estimations of formation surface texture.

Present tools contain transducers having significant reverberations that interfere with signal interpretation. Some open-hole scanning transducers have step focusing which gives reverberations in the lens itself. In addition, focused caliper standoff transducers have undesirable reverberations from plastic lenses. The caliper/standoff transducers have radiation patterns which lose echoes for certain eccentered configurations.

Open hole scanning transducers also need a transducer with less reverberation to operate in heavier muds than can be investigated with the transducers now available. The logging while drilling, formation speed of sound, and caliper standoff tools also need an improved transducer to reduce loss of signal for eccentered tools in the borehole, to investigate smaller standoffs and to handle heavier weight muds.

Therefore, there is still a need for transducers that do not suffer from the deficiencies of the prior art.

There is another need in the art for transducers with minimal reverberation.

There is even another need in the art for transducers that permit nearer standoff measurements, improved bond measurements and detection of thinner cement layers behind the casing.

These and other needs in the art will become apparent to those of skill in the art upon review of this specification, including its drawings and claims.

SUMMARY OF THE INVENTION

It is an object of the present invention to provide for transducers that do not suffer from the deficiencies of the prior art.

It is another object of the present invention to provide for transducers with minimal reverberation.

It is even another object of the present invention to provide for transducers that permit nearer standoff measurements, improved cement bond measurements and detection of thinner cement layers behind the casing.

These and other objects of the present invention will become apparent to those of skill in the art upon review of this specification, including its drawings and claims.

In one embodiment of the present invention there is provided a transducer package including an unpoled piezoelectric lens bonded to an active piezoelectric element.

According to another embodiment of the present invention there is provided a transducer package including a metal faceted lens bonded to an active piezoelectric material. A multi-element transducer package comprising:

According to even another embodiment of the present invention there is provided a multi-element transducer package including a first transducer unit comprising a first wedge bonded a first poled piezoelectric element bonded to a first backing, a middle transducer unit comprising a second poled piezoelectric element bonded to a second backing, a second transducer unit comprising a second wedge bonded to a third poled piezoelectric element bonded to a third backing. In this embodiment, the first and second units are bonded to the middle unit such that the piezoelectric elements are isolated from each other.

These and other embodiments of the present invention will become apparent to those of skill in the art upon review of this specification, including its drawings and claims.

DETAILED DESCRIPTION OF THE INVENTION

The transducer materials and packaging of the present invention reduce reverberation. By minimizing the reverberation of a transducer, the minimum inspection distance can be decreased thereby permitting nearer standoff measurements, improved bond measurements, detection of thinner cement layers behind the casing, and better estimations of formation surface texture. The transducers of the present invention find utility in both wireline and logging while drilling applications.

In the first embodiment of the present invention, the transducer lens is made of unpoled piezoelectic material. Lenses made of this material provide for better impedance matching between the lens and the active piezoelectric thereby reducing reverberation. In addition, the lenses made of unpoled piezoelectic material have larger speed of sound which allows for shorter focal lengths than the current lenses made of epoxy.

Figure 1:
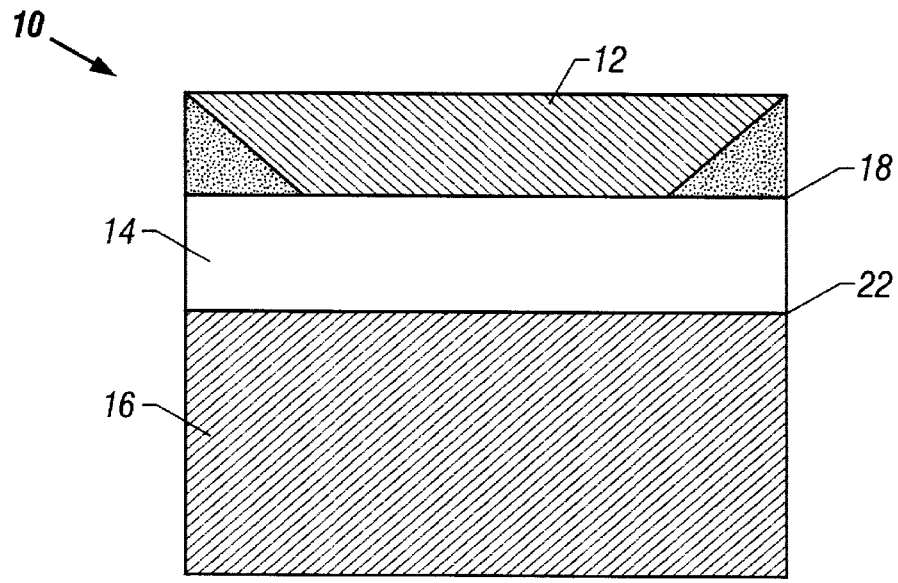
FIG. 1 is a cut away view of one embodiment of transducer package 10 showing unpoled piezoelectric lens 12, active piezoelectric disk 14 and backing 16.
Figure 2:
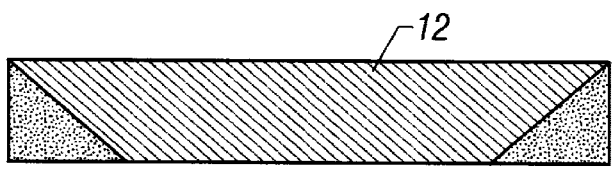
FIG. 2 is a cut away view of unpoled piezoelectric lens 12 of FIG. 1
Figure 3:
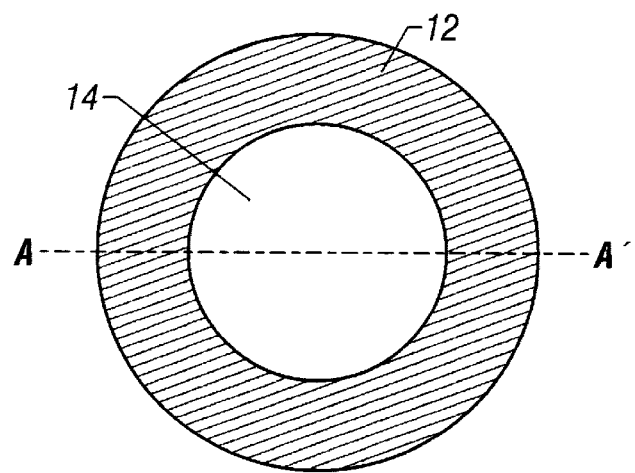
FIG. 3 is a top view of transducer package 10 of FIG. 1.

Referring now to FIGS. 1–3, a first embodiment of a transducer package providing reduced reverberation will be shown and described in detail. FIG. 1 is a cut away view of a transducer package, shown generally as 10, utilizing an unpoled piezoelectric lens 12. FIG. 2 is a cut away view of unpoled piezoelectric lens 12 of FIG. 1 as purchased from a piezoelectric manufacturer. FIG. 3 is a top view of transducer package 10 of FIG. 1.

Transducer package 10 generally includes unpoled piezoelectric lens 12 bonded to active piezoelectric element 14 bonded to absorbive backing 16. Both unpoled and active piezoelectric material are commercially available from a piezoelectric manufacturer. Non-limiting examples of suitable commercially available piezoelectric material include lead metaniobate and lead zirconate titanate.

Backing 16 may be any suitable material, capable of withstanding downhole temperatures. Preferably, backing 16 is a material having an acoustic impedance similar to that of the piezoelectric material being used. More preferably, backing 16 is a tungsten loaded epoxy or a tungsten loaded rubber as are known to those skilled in the art.

Unpoled piezoelectric lens 12 is bonded to active piezoelectric element 14 at bonding layer 18 by any suitable adhesive capable of withstanding downhole temperatures. Because of matched thermal expansion coefficients of the lens 12 and active element 14, the bonding layer 18 be made with commercially available epoxy adhesives.

Piezoelectric element 14 is bonded to backing 16 at bonding layer 22 by suitable means capable of withstanding downhole temperatures. Preferably, bonding layer 22 is a high temperature epoxy adhesive commercially available for bonding metal to glass.

Once bonding layers 18 and 22 are placed between unpoled piezoelectric lens 12 and active piezoelectric element 14 and between active piezoelectric element 14 and backing 16 respectively, transducer 10 is clamped together and the bonding layers allowed to cure as is known in the art. Once bonded together, transducer 10 is potted in epoxy, with the thickness of the epoxy layer dependent upon and matched to the impedance of the material transmitting through, as is known in the art.

Figure 4:
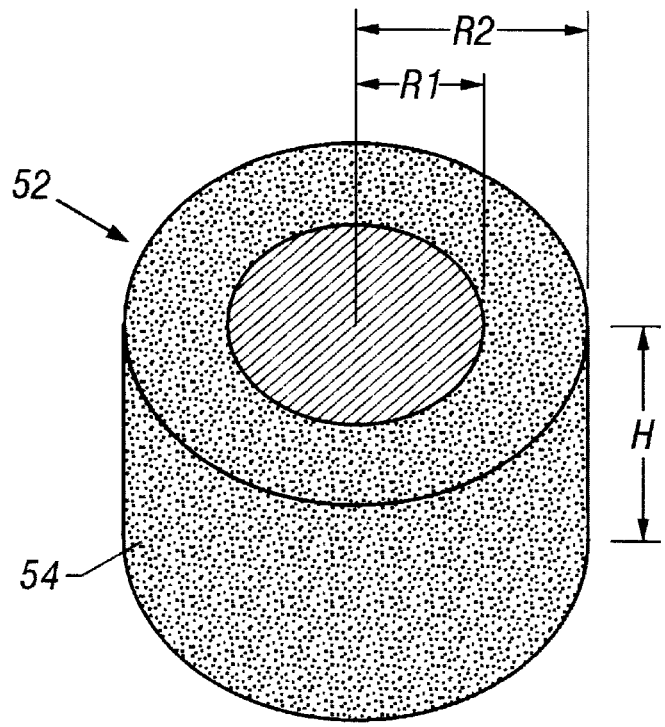
FIG. 4 is view of aluminum shell 52 having height h, inner radius r1 and radius r2 prior to machining to form acoustic len 50.
Figure 5A:
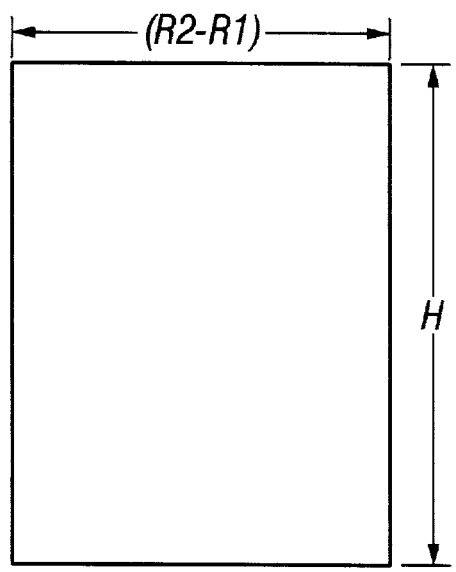
FIG. 5a is a cross section of portion 54 (r2–r1) of shell 52 before machining.
Figure 5B:
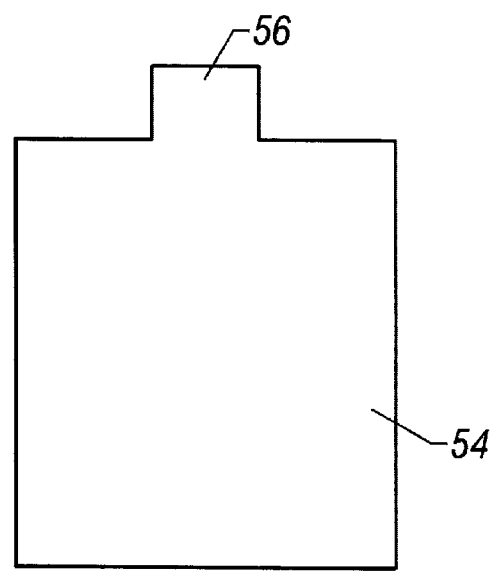
FIG. 5b is a cross section of shell 52 after the first machine cut to form retaining ring 56.
Figure 6A:
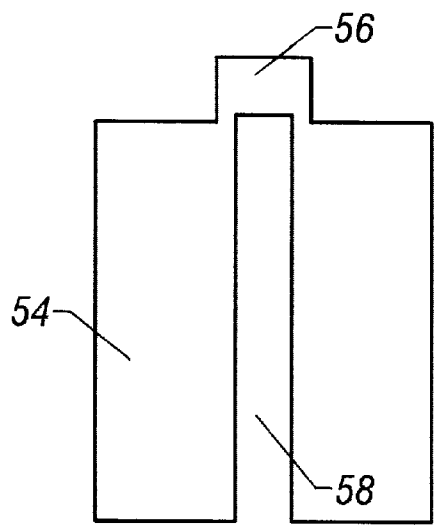
FIG. 6a is a cross section of shell 52 after machining of groove 58.
Figure 6B:
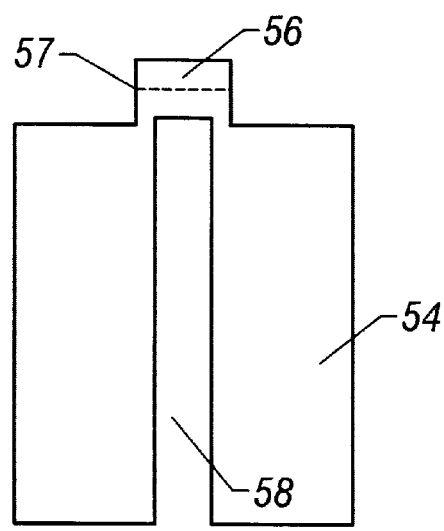
FIG. 6b is a cross section of shell 52 after machining radial slots.
Figure 7:
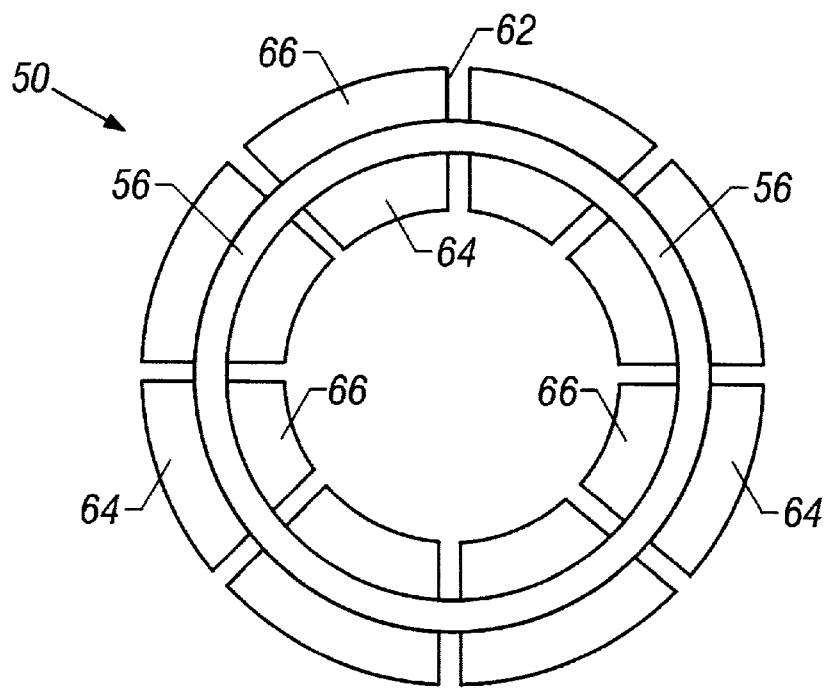
FIG. 7 is a Top view of shell 52 after machining in preparation for bonding to active piezoeletric material (not shown).
Figure 8:
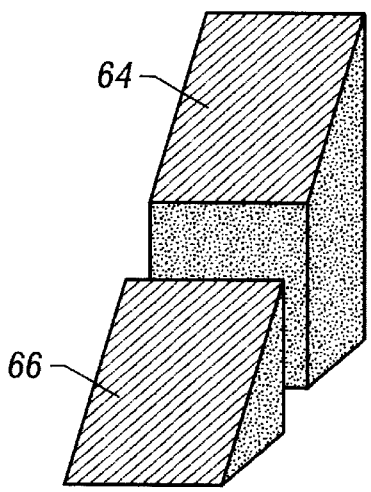
FIG. 8 is a view of aluminum lens 50 facet after bonding piezoelectric and after machining while bonded to piezoelectric.

A second embodiment of the transducer of the present invention includes a metal faceted lens to minimize reverberation time after firing. Preferably, the metal lens is impedance matched to the piezoelectric material. For a non-limiting example, aluminum offers impedance matching for lead metaniobate. Aluminum also offers ease of machining and of assembly and allows for thinner lenses than those made of unpoled piezoelectic material or epoxy. For another non-limiting example, titanium offers impedance matching for lead zirconate titanate Referring now to FIGS. 4–8 this second embodiment of a transducer package will be shown and described in detail. FIG. 4 is a view of aluminum shell 52 having height h, inner radius R1 and radius R2 prior to machining to form an acoustic lens. FIG. 5a is a cross section of portion 54 (R2–R1) of shell 52 before machining and FIG. 5b is a cross section of shell 52 after the first machine cut to form retaining ring 56. FIG. 6a is a cross section of shell 52 after machining of groove 58 and FIG. 6b is a cross section of shell 52 with hidden line 57 showing the top of the radial slots after machining. FIG. 7 is a top view of shell 52 after machining in preparation for bonding to active piezoeletric material (not shown). FIG. 8 is a view of aluminum lens facet after bonding to piezoelectric and after machining while bonded to piezoelectric.

Referring to FIG. 4, aluminum lens 50 is machined from cylindrical aluminum shell 52 which includes outer portion 54. Before machining, shell 52 has physical dimensions of height h, inner radius R1 and radius R2. The dimensions of h, R1 and R2 are selected to provide the desired focal distances as is known in the art.

Referring to FIG. 5a, outer section 54 of shell 52 has a cross section of R2–R1. In forming lens 50, a retaining ring 56 is first machined into shell 52 such that outer section 54 of shell 52 has a cross section (R2–R1) as shown in FIG. 5b.

Referring to FIG. 6a, next a circumferential groove 58 is machined into outer section 54 of shell 52 such that outer section 54 has a cross section (R2–R1). Radial grooves or slots 62 are then machined from the bottom of shell 54 such that the top view of shell 52 is as shown in FIG. 7 with retaining ring 56 being the only material connecting inner-aluminum sectors 64 and outer-aluminum sectors 66 together.

Shell 52 as shown in FIG. 7 is bonded to the active piezoelectric element (not shown) by any suitable adhesive capable of withstanding downhole temperatures. Preferably, the adhesive is an epoxy adhesive rated for bonding metal to glass. The small size of the facets reduces bonding problems due to differential thermal expansion between metal and piezoelectric. The piezoelectric material may be any material which may be matched in acoustic impedance to commercially available metals. Non-limiting examples of suitable commercially available piezoelectric material and matching metals include lead metaniobate with aluminum and lead zirconate titanate with titanium.

After bonding to the active piezoelectric element the top part of aluminum sectors 64 are machined away at an angle such that inner-aluminum sectors 64 and outer-aluminum sectors 66 are wedged shaped as shown in FIG. 8.

The active piezoelectric element, now bonded to aluminum faceted lens 50, is then bonded to backing (not shown). The backing may be any suitable material, capable of withstanding downhole temperatures. Preferably, the backing is a material having an acoustic impedance similar to that of the piezoelectric material being used. More preferably, backing 16 is a tungsten loaded epoxy or a tungsten loaded rubber as are known to those skilled in the art.

Preferably, aluminum faceted lens 50 is bonded to a backing by a commercially available adhesive, capable of withstanding downhole temperatures and capable of boding metal to glass.

The completed package is then potted in epoxy, with the thickness of the epoxy layer dependent upon and matched to the impedance of the material transmitting through, as is known in the art. Potting in this manner results in the gaps between the aluminum sectors 64 and 66 being filled with epoxy.

Sectors 64 and 66 may be of any suitable size to prevent the active piezoelectric element from being shattered by the differential thermal expansion of the metal and the ceramic. Preferably, the dimensions of the sectors are chosen to be smaller than an acoustical wavelength.

While facets 64 and 66 of lens 50 of second embodiment were formed of aluminum, it is understood that the facets can be machined or assembled from other suitable materials. Preferably, facets 64 and 66 are formed from a material having an acoustic impedance closely matched to that of the piezoelectric element. For example aluminum facets have an acoustic impedance similar to that of the piezoelectric lead metaniobate, and titanium facets have an acoustic impedance similar to that of the piezoelectric lead zirconate titanate. In addition, facets 64 and 66 may be made from unpoled piezoelectric material which provides the advantage of versatility in lens geometries.

A third embodiment of the transducer of the present invention includes a new acoustic isolator design which permits pitch-catch operation. In this embodiment, the transmitter backing is only weakly coupled to the receiver piezoelectric thereby reducing reverberation and improving signal to noise ratio. This embodiment is especially important in logging while drilling transducers which require relatively short backing materials to avoid machining large holes which unacceptably weaken the drill collar. The new isolator design allows multiple elements for multiple direction radiation patterns which helps to avoid the loss of wall echoes when the tool is eccentered in the borehole. In addition, transducers packaged in this manner find utility in the cement imaging system.

Figure 9:
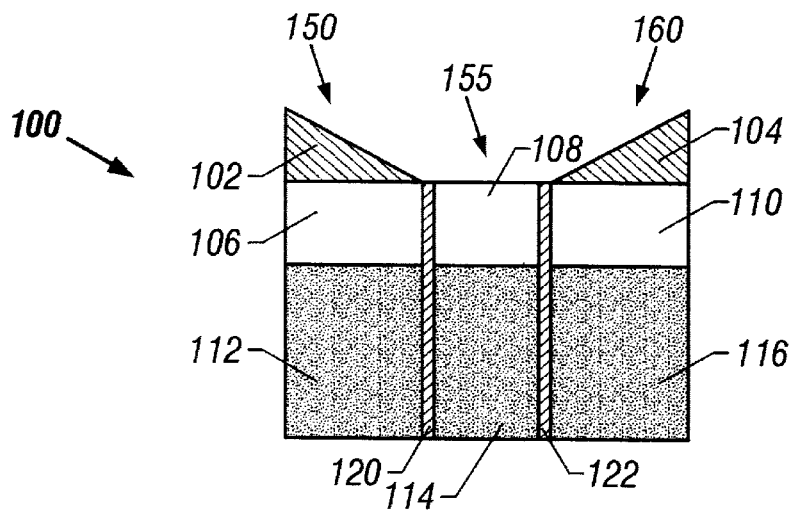
FIG. 9 is a cross sectional view of multi-element transducer 100, having unpoled piezoelectric wedges 102 and 104, poled active piezoelectric sections 106, 108 and 110, backing material 112, 114 and 116, and acoustic isolator 120 and 122.
Figure 10:
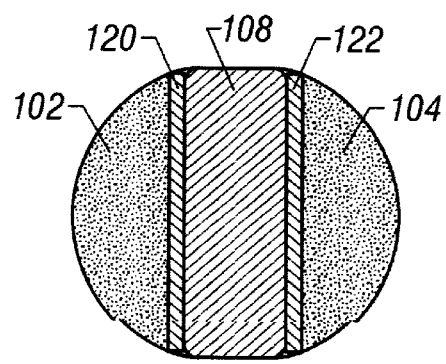
FIG. 10 is a top view of transducer package 100 of FIG. 9.
Figure 11:
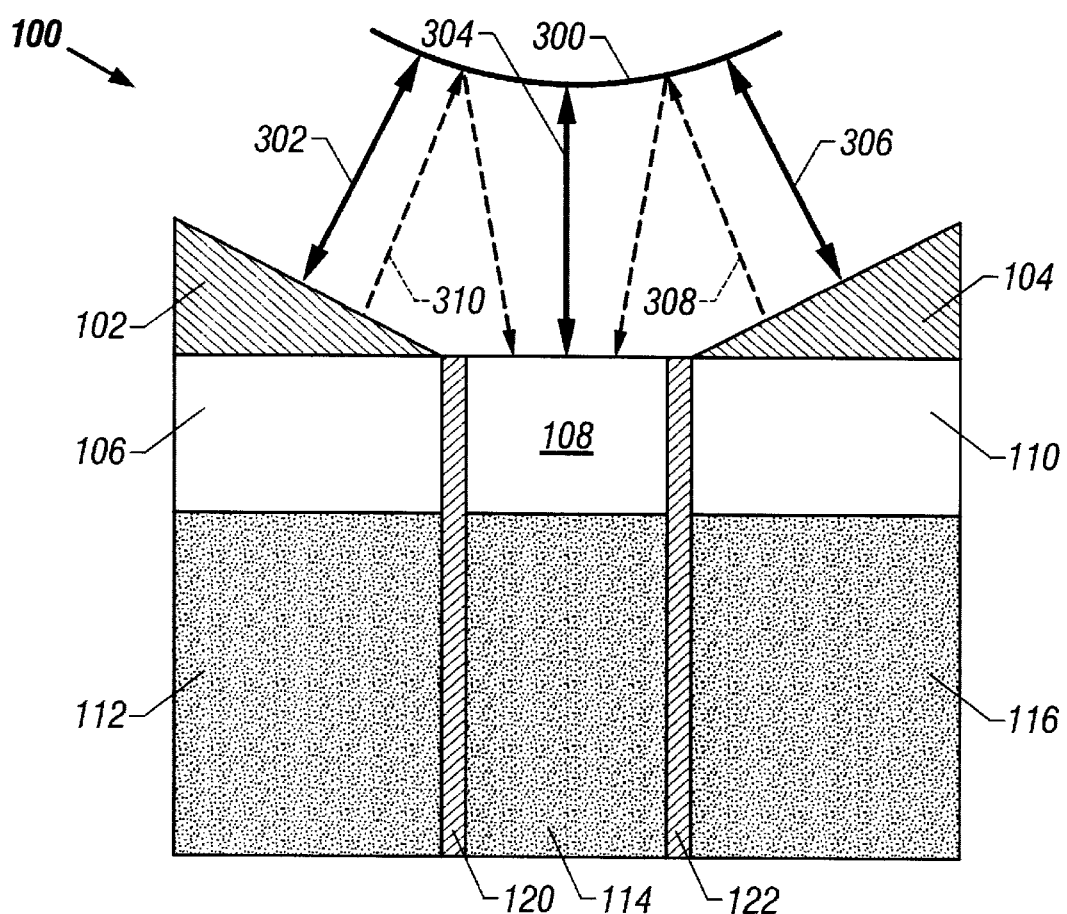
FIG. 11 is a cross-sectional view of the propagation directions for transducer 100 of FIG. 9.

Referring now to FIGS. 9–11 a third embodiment of a transducer package providing reduced reverberation will be shown and described in detail. FIG. 9 is a cross sectional view of a multi-element transducer, shown generally as 100, having unpoled piezoelectric wedges 102 and 104, poled active piezoelectric sections 106, 108 and 110, backing material 112, 114 and 116, and acoustic isolator 120 and 122. FIG. 10 is a top view of transducer package 100 of FIG. 9. FIG. 11 is a cross-sectional view of the propagation directions for transducer 100 of FIG. 9.

Transducer package 100 generally includes three active piezoelectric elements 106, 108 and 110 having individual backing 112, 114 and 116 respectfully. Element 106 is completely separated from elements 108 and 110 by acoustic isolator 120 and element 110 is completely separated from elements 108 and 106 by acoustic isolator 122 as shown in FIG. 10.

Active piezoelectric material for sections 106, 108 and 110 are commercially available from a piezoelectric manufacturer. Non-limiting examples of suitable commercially available piezoelectric material include lead metaniobate and lead zirconate titanate.

Backings 112, 114 and 116 may be any suitable material, capable of withstanding downhole temperatures. Preferably, the backing will attenuate acoustic waves from the backing side of the active piezoelectric element so that the reverberation of such waves in such backing are attenuated. Even more preferably, the backings are a material having an acoustic impedance similar to that of the piezoelectric material being used. More preferably, the backings are a tungsten loaded epoxy or a tungsten loaded rubber as are known to those skilled in the art.

During assembly of transducer 100, individual active piezoelectric elements 106, 108 and 110 are bonded to backings 112, 114 and 116, and unpoled piezoelectric wedges are bonded to active elements 106 and 110 to form three single units 150, 155 and 160. Preferably, elements 106, 108 and 110 are bonded to backings 112, 114 and 116 by a commercial adhesive capable of withstanding downhole temperatures and bonding metal to glass.

Single units 150, 155 and 160 are then tacked together with small bridges made of the epoxy used for potting with the bridges establishing the thickness of isolators 120 and 122. When package 100 is potted with epoxy, the epoxy fills the gaps established by the bridges, forming uniform thickness isolators. The thickness of the epoxy layer being dependent upon and matched to the impedance of the material transmitting through, as is known in the art.

Referring now to FIG. 11, transducer 100 can be used for either pulse-echo or pitch-catch operation. Wedges 102 and 104 permit pulse-echo detection of surfaces which are not perpendicular to the cylindrical axis of the transducer. This feature is important for eccentered LWD tools in the borehole. For example, as shown in FIG. 11, pulse echo propagation off boundary 300 may occur in directions 302, 304 and 306 (3 places) and pitch catch propagation off boundary 300 can occur in directions 308 and 310 (2 places).

The high frequency (0.4 MHz to 2 MHz) center transducer unit 155 can detect walls at very short standoffs. For heavy weight muds, however, high frequency signals are attenuated, limiting radial range to about 1 inch. For greater radial distances, the outer transmitter units 150 and 160 have stacked piezoelectric elements to generate powerful signals. The outer elements 106 and 110 are designed to operate at lower frequencies (100 KHz to 300 KHz) than the center transducer 108.

Since the attenuation per wavelength is essentially constant, range increases inversely with transmitter frequency. The long ringdown reverberations of low frequency transducers 150 and 160 prevent detecting echoes for approximately the first inch of radial travel. The high frequency element 155, however, covers the range from 0.3 to 1 inch for all muds. As a receiver, the high frequency element 155 has flat response throughout the spectral range of the low frequency transducers. Furthermore, in pitch-catch operation, the high frequency receiver 155 is decoupled from the backing reverberations of the low frequency transmitters 150 and 160, giving good signal to noise ratio. For greatest radial range, the broad radiation patterns of the low frequency transducers 150 and 160 give strong signals in the center receiver 155 when both low frequency transmitters 150 and 160 are fired simultaneously.

Figure 12:
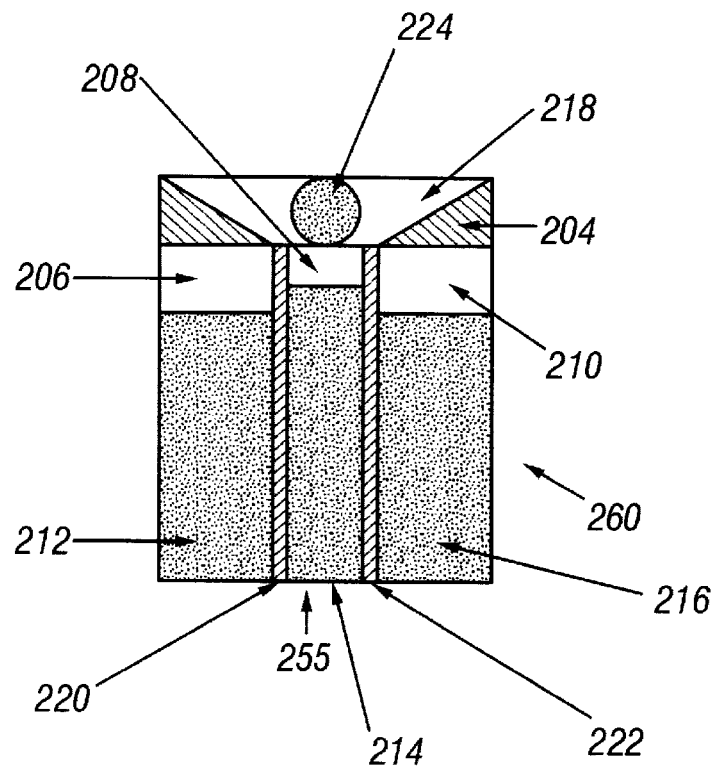
FIG. 12 is a cross sectional view of multi-element transducer 200, having unpoled piezoelectric wedges 202 and 204, poled active piezoelectric sections 206, 208 and 210, piezoelectric for fluid velocity 224, backing material 212, 214, 216 and 218 and acoustic isolator 220 and 222.
Figure 13:
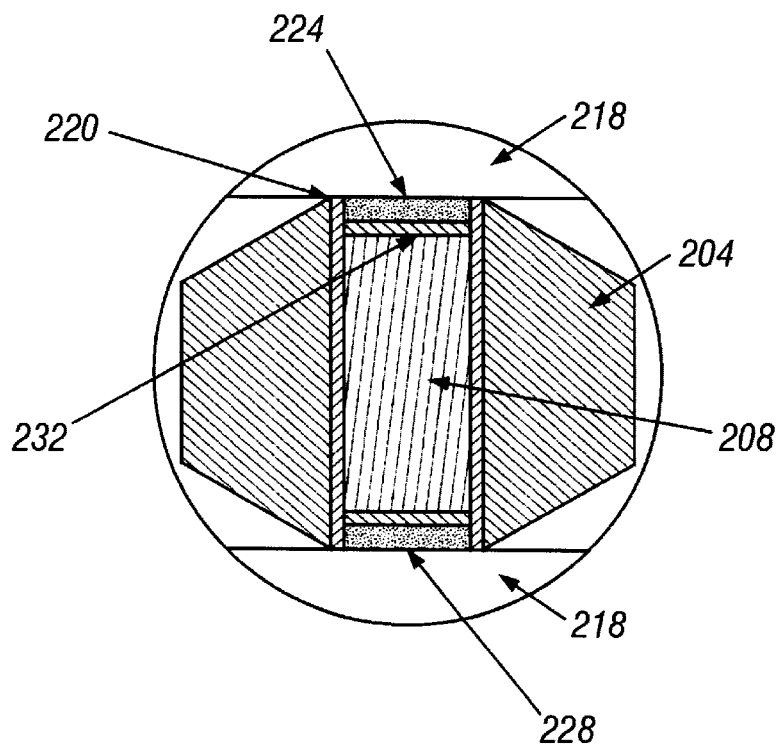
FIG. 13 is a top view of multi-element transducer 200 of FIG. 12.
Figure 14:
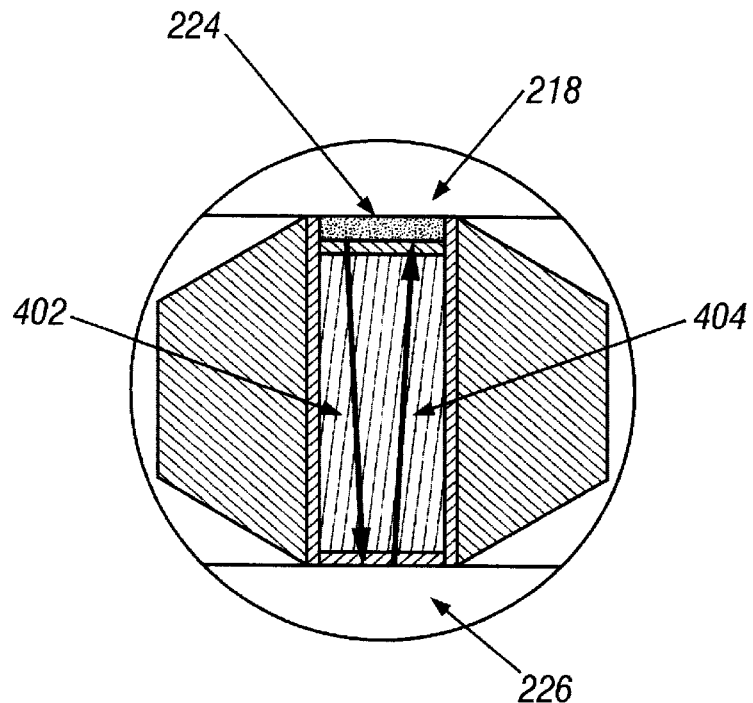
FIG. 14 is a top view of multi-element transducer 200 of FIG. 12 illustrating pulse-echo acoustic path 402 and 404.
Figure 15:
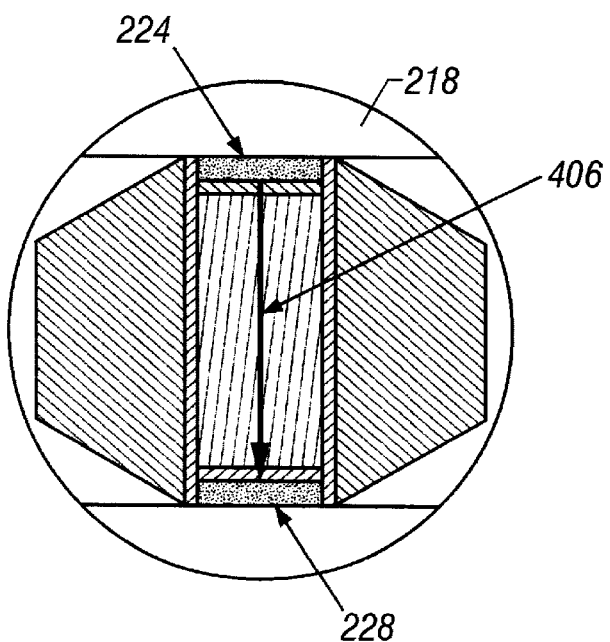
FIG. 15 is a top view of multi-element transducer 200 of FIG. 12 illustrating pitch-catch acoustic path 406.

Referring now to FIGS. 12–15, a fourth embodiment of a transducer package for measuring fluid velocity providing reduced reverberation will be shown and described in detail. FIG. 12 is a cross sectional view of multi-element transducer 200, having unpoled piezoelectric wedges 202 and 204, poled active piezoelectric sections 206, 208 and 210, piezoelectric for fluid velocity 224, backing material 212, 214, 216 and 218 and acoustic isolators 220 and 222. FIG. 13 is a top view of transducer package 200 of FIG. 12. FIG. 14 is top view of transducer package 200 of FIG. 12 showing the pulse-echo acoustic path. FIG. 15 is top view of transducer package 200 of FIG. 12 showing the pitch-catch acoustic path.

Referring to FIGS. 12 and 13, transducer package 200 generally includes active piezoelectric elements 206, 208 and 210 having individual backing 212, 214 and 216 respectfully. Element 206 is completely separated from elements 208 and 210 by acoustic isolator 220 and element 210 is completely separated from elements 208 and 206 by acoustic isolator 222. Transducer package 200 also includes piezoelectric element 224.

Referring now additionally to FIG. 14, for pulse-echo operation, transducer package 200 includes transmitter receiver element 224 and acoustic reflector 226. Referring now additionally to FIG. 15, for pitch-catch operation, transducer package 200 includes transmitter piezoelectric element 224 and receiver piezoelectric element 228. Elements 224 and 228, when utilized, are also completely isolated from elements 206, 208 and 210 by insulators 220, 222 and 232.

Active piezoelectric material for elements 206, 208 210, 224 and 228 are commercially available from a piezoelectric manufacturer. Non-limiting examples of suitable commercially available piezoelectric material include lead metaniobate and lead zirconate titanate.

Backings 212, 214 216 and 218 may be any suitable material, capable of withstanding downhole temperatures.

Preferably, the backings are a material having an acoustic impedance similar to that of the piezoelectric material being used. More preferably, the backings are a tungsten loaded epoxy or a tungsten loaded rubber as are known to those skilled in the art.

During assembly of transducer 200, individual active piezoelectric elements 206, 208 and 210 are bonded to backings 212, 214 and 216, and unpoled piezoelectric wedges are bonded to active elements 206 and 210 to form three single units 250, 255 and 260. Piezoelectric elements 224 and 228 or piezoelectric element 224 and acoustic reflector 226 are bonded to backing 218 and tacked to piezoelectric element 208 with small bridges made of the epoxy used for potting with the bridges establishing the thickness of insulator 232. Preferably, elements 206, 208, 210, 224 and 228, when utilized, are bonded to backings 212, 214, 216 and 218 by a commercial adhesive capable of withstanding downhole temperatures and bonding metal to glass.

Single units 250, 255 and 260 are tacked together with small bridges made of the epoxy used for potting with the bridges establishing the thickness of isolators 220 and 222. When package 200 is potted with epoxy, the epoxy fills the gaps established by the bridges, forming isolators 220 and 222 with each insulator being of uniform thickness. The thickness of the epoxy layer being dependent upon and matched to the impedance of the material transmitting through, as is known in the art.

Referring now to FIGS. 14 and 15, transducer 200 can be used for either pulse-echo or pitch-catch operation. Referring to FIG. 14 there is shown an illustration of the pulse-echo acoustic path for transducer 200. In this configuration, piezoelectric element 224 is a transmitter/receiver. The signal is transmitted along acoustic path 402, reflected off acoustic reflector 226 and received along acoustic path 404.

Referring to FIG. 15 there is shown an illustration of the pitch-catch acoustic path for transducer 200. In this configuration, piezoelectric element 224 is a transmitter piezoelectric and piezoelectric element 228 is a receiver piezoelectric. The signal is transmitted from element 224 along acoustic path 406 and received by element 228.

As with embodiment 100 of the present invention, the outer elements 206 and 210 are designed to operate at lower frequencies than the center transducer 208. Preferably, the elements 206 and 210 operate in the range of between about 100 KHz and about 300 KHz and elements 208 and 224 operate in the range of between about 0.4 MHz and about 2 MHz.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

What is claimed is:

1. A transducer package comprising:
   (a) and active piezoelectric element;
   (b) an unpooled piezoelectric lens bonded to the active pieozoelectric element; and
   (c) an epoxy layer surrounding elements (a) and (b), wherein the thickness of the epoxy layer is dependent upon and matched to the acoustic impendance of a material being transmitted through.

2. A transducer package comprising:
(a) and active piezoelectric element;
(b) an unpooled piezoelectric lens bonded to the active pieozoelectric element;
wherein the piezoelectric element and lens comprise a material selected from the group consisting of lead metaniobatye and lead zirconate titanate.

3. A transducer package comprising:
(a) and active piezoelectric element;
(b) a metal faceted lens bonded to the active piezoelectric element; and
(c) an epoxy layer surrounding elements (a) and (b),
wherein the thickness of the epoxy layer is dependent upon and matched to the impedance of a material being transmitted through.

4. The transducer package of claim 3 wherein the metal faceted lens is formed from a material selected from the group consisting of aluminum, titanium and unpoled-piezoelectric material.

5. The transducer package of claim 3 wherein the piezoelectric element is a material selected from the group consisting of lead metaniobate and lead zirconate titanate.

6. A multi-element transducer package comprising:
(a) a first transducer unit comprising a first wedge bonded to a first poled piezoelectric element bonded to a first backing;
(b) a middle transducer unit comprising a second poled piezoelectric element bonded to a second backing; and
(c) a second transducer unit comprising a second wedge bonded to a third poled piezoelectric element bonded to a third backing;
wherein the first and second units are bonded to the middle unit such that the piezoelectric elements are isolated from each other; and
wherein the backing material has an acoustic impedance similar to the piezoelectric elements.

7. The multi-element transducer package of claim 6 wherein the first and second wedges are formed from materials selected from the group consisting of unpoled piezoelectric and metal.

8. The multi-element transducer package of claim 6 wherein the middle transducer unit operates a frequency between about 400 and about 2000 Khz and wherein the first and the second transducer units operate between about 100 and about 300 Khz.

9. The multi-element transducer of claim 6 wherein the first transducer unit and the second transducer unit include stacked active piezoelectric elements.

10. The multi-element transducer package of claim 6 further comprising:
(d) a piezoelectric transmitter for fluid velocity bonded to a backing at a first end of the middle transducer unit such that the transmitter is isolated from the piezoelectric elements; and
(e) an acoustic reflector bonded to a backing at a second end the middle transducer unit.

11. The transducer package of claim 10 wherein the piezoelectric elements comprise a material selected from the group consisting of lead metaniobate and lead zirconate titanate.

12. The multi-element transducer package of claim 6 further comprising:
(d) a piezoelectric transmitter for fluid velocity bonded to a backing at a first end of the middle transducer unit such that the transmitter is isolated from the piezoelectric elements; and
(e) a piezoelectric receiver bonded to a backing at a second end the middle transducer unit.

13. The transducer package of claim 12 wherein the piezoelectric elements comprise a material selected from the group consisting of lead metaniobate and lead zirconate titanate.

14. The transducer package of claim 1 further comprising:
(d) a backing material bonded to the active piezoelectric element,
wherein the piezoelectric element is located between the backing layer and the piezoelectric lens,
wherein the piezoelectric element and the piezoelectric lens each have an acoustic impedance, and
wherein the backing material has an acoustic impedance similar to the acoustic impedance of the piezoelectric element and of the piezoelectric lens.

15. The transducer package of claim 1 wherein the piezoelectric element and lens comprise a material selected from the group consisting of lead metaniobate and lead zirconate titanate.

16. The transducer package of claim 2 further comprising:
(c) an epoxy layer surrounding elements (a) and (b),
wherein the thickness of the epoxy layer is dependent upon and matched to the impedance of a material being transmitted through.

17. The transducer package of claim 2 further comprising:
(d) a backing material bonded to active piezoelectric element,
wherein the piezoelectric element is located between the backing layer and the piezelectriclens,
wherein the piezoelectric element and the piezelectric lens each have an acoustic impedance, and
wherein the backing material has an acoustic impedance similar to the acoustic impedance of the piezoelectric element and of the piezoelectric lens.

18. The transducer package of claim 3 further comprising:
(e) a backing material bonded to the active piezoelectric element,
wherein the piezoelectric element is located between the backing layer and the metal faceted lens,
wherein the metal faceted lens has an acoustic impedance, and
wherein the active piezoelectric element has an acoustic impedance similar to that of the metal faceted lens.

* * * * *